United States Patent
Nikolaev et al.

(10) Patent No.: US 12,169,883 B2
(45) Date of Patent: Dec. 17, 2024

(54) ACCELERATED FILTERED BACK PROJECTION FOR COMPUTED TOMOGRAPHY IMAGE RECONSTRUCTION

(71) Applicant: Smart Engines Service, LLC, Moscow (RU)

(72) Inventors: Dmitry Petrovich Nikolaev, Moscow (RU); Anastasiya Dolmatova, Perm (RU); Marina Chukalina, Moscow (RU)

(73) Assignee: Smart Engines Service, LLC, Moscow (RU)

(*) Notice: Subject to any disclaimer, the term of this patent is extended or adjusted under 35 U.S.C. 154(b) by 619 days.

(21) Appl. No.: 17/405,732

(22) Filed: Aug. 18, 2021

(65) Prior Publication Data

US 2022/0165001 A1    May 26, 2022

(30) Foreign Application Priority Data

Nov. 23, 2020 (RU) ................. 2020138293

(51) Int. Cl.
*G06T 11/00* (2006.01)
*A61B 6/03* (2006.01)
*G01N 23/046* (2018.01)

(52) U.S. Cl.
CPC ............. *G06T 11/006* (2013.01); *A61B 6/032* (2013.01); *G01N 23/046* (2013.01); *G01N 2223/419* (2013.01); *G06T 2207/10081* (2013.01); *G06T 2207/20061* (2013.01); *G06T 2211/421* (2013.01)

(58) Field of Classification Search
CPC ............. G06T 11/006; G06T 2211/421; G06T 2207/20061; G06T 2207/10081; A61B 6/032; G01N 23/046; G01N 2223/419
See application file for complete search history.

(56) References Cited

U.S. PATENT DOCUMENTS

| | | | |
|---|---|---|---|
| 9,524,567 B1* | 12/2016 | Brokish | A61B 6/5205 |
| 2003/0190065 A1* | 10/2003 | Hamill | G01T 1/2985 |
| | | | 382/131 |
| 2010/0002955 A1* | 1/2010 | George | G06T 11/006 |
| | | | 382/280 |

OTHER PUBLICATIONS

Potts et al., "New Fourier reconstruction algorithms for computerized tomography", Dec. 2000, SPIE, Proc. SPIE Wavelet Applications in Signal and Image Processing VIII, vol. 4119, p. 13-23. (Year: 2000).*

Prun et al., "A Computationally Efficient Version of the Algebraic Method for Computer Tomography", Oct. 2013, Springer, Automation and Remote Control, vol. 74, p. 1670-1678. (Year: 2013).*

(Continued)

*Primary Examiner* — Vincent Rudolph
*Assistant Examiner* — Timothy Choi
(74) *Attorney, Agent, or Firm* — Procopio, Cory, Hargreaves & Savitch LLP (57) ABSTRACT

Accelerated filtered back projection for computed tomography image reconstruction. In an embodiment, a filtered back projection is performed on a sinogram. The back projection may comprise transitioning the sinogram to a linogram using linear interpolation, and performing an inverse Fast Hough Transform on the linogram to produce a reconstructed CT image. Filtering in the filtered back projection may use an infinite impulse response (IIR) filter.

12 Claims, 4 Drawing Sheets

(56) References Cited

OTHER PUBLICATIONS

Brandenstein et al., "Least-Squares Approximation of FIR by IIR Digital Filters", Jan. 1998, IEEE, Transactions On Signal Processing, vol. 46, No. I, p. 21-30. (Year: 1998).*

Edmonson et al., "A Global Least Mean Square Algorithm for Adaptive IIR Filtering", Mar. 1998, IEEE, Transactions On Circuits and Systems-II: Analog and Digital Signal Processing, vol. 45, No. 3, p. 379-384. (Year: 1998).*

Gao et al., "Implementing the Nelder-Mead simplex algorithm with adaptive parameters", 2012, Springer, Computational Optimization and Applications, vol. 51, p. 259-277. (Year: 2012).*

Hull et al., "Block Adaptive IIR Filters Using Preconditioned Conjugate Gradients for Orthogonalization", May 1995, IEEE, 1995 International Conference on Acoustics, Speech, and Signal Processing, p. 1384-1387. (Year: 1995).*

Ershov et al., "Generalization of the Fast Hough Transform for Three-Dimensional Images", Jul. 2018, Springer, Mathematical Models and Computational Methods, vol. 63, p. 626-636. (Year: 2018).*

Dolmatova et al., "Accelerated FBP for Computed Tomography Image Reconstruction", Sep. 2020, IEEE, 2020 IEEE International Conference on Image Processing (ICIP), p. 3030-3034. (Year: 2020).*

Edholm et al., "Image Reconstruction from Linograms: Implementation and Evaluation", Sep. 1988, IEEE, IEEE Transactions On Medical Imaging, vol. 7, No. 3, p. 239-246. (Year: 1988).*

Clackdoyle, "Data Consistency for Linograms and Planograms", Jul. 2018, IEEE, IEEE Transactions On Radiation and Plasma Medical Sciences, vol. 2, No. 4, p. 288-299. (Year: 2018).*

Geoffrey D. Rubin, MD, "Computed Tomography: Revolutionizing the Practice of Medicine for 40 Years," Radiology: vol. 273: No. 2 (Suppl)—Nov. 2014, pp. 45-74.

H.A. H.A. et al., Смелкина РАСПОЗНАВАНИЕ ЭМФИЗЕМЫ ЛЁГКИХ ПО ДАННЫМ КОМПЬЮТЕРНОЙ ТОМОГРАФИИ, Распознавание эмфиземы лёгких по данным компьютерной томографии, Компьютерная оптика том №5, No. 5, pp. 726-731.

Luc Salvo et al., "3D imaging in material science: Application of X-ray tomography," C. R. Physique 11 (2010) 641-649.

Jose Baruchel et al., "X-Ray Tomography in Material Science," HERMES Science Publications, Paris, 2000, ISBN 2-7462-0115-1, 209 pages.

E.H. E.H et al., " Симонов АНАЛИЗ ТРЕХМЕРНЫХ АЛГОРИТМОВ РЕКОНСТРУКЦИИ В РЕНТГЕНОВСКОЙ КОМПЬЮТЕРНОЙ ТОМОГРАФИИ ," Bulletin of the South Ural State University. Ser. Computer Technologies, Automatic Control, Radio Electronics, 2017, vol. 17, No. 2, pp. 24-32.

D. Potts et al., "New Fourier reconstruction algorithms for computerized tomography," Medical University of Lubeck, Institute of Mathematics, 11 pages.

Daniel Potts, "Fourier reconstruction of functions from their non-standard sampled Radon transform," 2000 Mathematics Subject Classification. 44A12, 65T50, pp. 1-21.

Fredrik Andersson, "Fast Inversion of the Radon Transform Using Log-Polar Coordinates and Partial Back-Projections," 2005 Society for Industrial and Applied Mathematics, Siam J. Appl. Math, vol. 65, No. 3, pp. 818-837.

Samit Basu et al., "O(N2 log2N) Filtered Backprojection Reconstruction Algorithm for Tomography," IEEE Transactions On Image Processing, vol. 9, No. 10, Oct. 2000, pp. 1760-1773.

Shu Xiao et al., "O(N2 log N) native fan-beam tomographic reconstruction," Conference Paper • Feb. 2002, DOI: 10.1109/ISBI.2002.1029386 • Source: IEEE Xplore, 5 pages.

Samit Basu et al., "Error Analysis and Performance Optimization of Fast Hierarchical Backprojection Algorithms," IEEE Transactions On Image Processing, vol. 10, No. 7, Jul. 2001, pp. 1103-1117.

G. N. Ramachandran et al., "Three-dimensional Reconstruction from Radiographs and Electron Micrographs: Application of Convolutions instead of Fourier Transforms," Proc. Nat. Acad. Sci. USA, vol. 68, No. 9, Sep. 1971, pp. 2236-2240.

Gengsheng L. Zeng, "Revisit of the Ramp Filter," IEEE Transactions On Nuclear Science, vol. 62, No. 1, Feb. 2015, pp. 131-136.

Rachid Deriche, "Using Canny's Criteria to Derive a Recursively Implemented Optimal Edge Detector," International Journal of Computer Vision, (1987) pp. 167-187.

Rachid Deriche, "Recursively Implementating the Gaussian and its Derivatives," RR-1893, INRIA. 1993, 26 pages.

M. J. D. Powell, "An efficient method for finding the minimum of a function of several variables without calculating derivatives," Applied Mathematics Group, Theoretical Physics Division, A.E.R.E. Harwell, Berks., pp. 155-162.

Fuchang Gao et al., "Implementing the Nelder-Mead simplex algorithm with adaptive parameters," Computational Optimization and Applications, May 2012, 20 pages.

Stefan Horbelt et al., "Discretization of the Radon Transform and of its Inverse by Spline Convolutions," IEEE Transactions On Medical Imaging, vol. 21, No. 4, Apr. 2002, pp. 363-376.

Paul R. Edholm et al., "Linograms in Image Reconstruction from Projections," IEEE Transactions on Medical Imaging, vol. MI-6, No. 4, Dec. 1987, pp. 301-307.

Martin L. Brady, "A Fast Discrete Approximation Algorithm for the Radon Transform," Siam J. Comput., vol. 27, No. 1, Feb. 1998, pp. 107-119.

E. I. Ershov et al., "Generalization of the Fast Hough Transform for Three-Dimensional Images," ISSN 1064-2269, Journal of Communications Technology and Electronics, 2018, vol. 63, No. 6, pp. 626-636.

V. E. Prun et al., "A Computationally Efficient Version of the Algebraic Method for Computer Tomography," ISSN 0005-1179, Automation and Remote Control, 2013, vol. 74, No. 10, pp. 1670-1678.

* cited by examiner

ACCELERATED FILTERED BACK PROJECTION FOR COMPUTED TOMOGRAPHY IMAGE RECONSTRUCTION

CROSS-REFERENCE TO RELATED APPLICATIONS

This application claims priority to Russian Patent App. No. 2020138293, filed on Nov. 23, 2020, which is hereby incorporated herein by reference as if set forth in full.

BACKGROUND

Field of the Invention

The embodiments described herein are generally directed to image reconstruction in computed tomography (CT), and, more particularly, to accelerated filtered back projection (FBP) for image reconstruction in computed tomography.

Description of the Related Art

X-ray computed tomography is a highly regarded technique for medical diagnostics, industrial quality control, material science research, and more. Filtered back projection is a commonly used technique in CT image reconstruction that demonstrates acceptable quality. Classical direct implementations of the FBP algorithm require the execution of $\Theta(N^3)$ operations, wherein N is the linear size of a two-dimensional CT slice (e.g., in pixels).

Meanwhile, rapid increases in the resolution of CT scanners have necessitated the processing of huge amounts of data. As a result, classical image reconstruction methods no longer satisfy current industry demands. Recent approaches, which include image reconstruction via the Fourier slice theorem, are better, but still require $\Theta(N^2 \log N)$ multiplication operations.

SUMMARY

Accordingly, systems, methods, and non-transitory computer-readable media are disclosed for accelerated filtered back projection for CT image reconstruction that can reconstruct a CT image in $\Theta(N^2 \log N)$ addition operations and $\Theta(N^2)$ multiplication operations.

In an embodiment, a method is disclosed that uses at least one hardware processor to reconstruct a computed tomography (CT) image by: performing a filtered back projection on a sinogram, wherein back projection in the filtered back projection comprises transitioning the sinogram to a linogram using linear interpolation, and performing an inverse Fast Hough Transform on the linogram to produce the reconstructed CT image, and wherein filtering in the filtered back projection uses an infinite impulse response (IIR) filter.

The method may further comprise using the at least one hardware processor to determine coefficients for the IIR filter by minimizing an error between an impulse response of the IIR filter and an impulse response of a finite impulse response (FIR) filter according to an optimization algorithm. The error may be a mean-square error. The optimization algorithm may comprise a simplex method. The optimization algorithm may comprise a conjugate gradient method.

The linogram may represent each line as two points (s, t) lying on boundaries of an N×N square area, wherein N is a linear size of the CT image. The linogram may comprise an N×N image for each of a plurality of types of lines, wherein the plurality of types of lines comprise mostly vertical lines with a positive shift, mostly vertical lines with a negative shift, mostly horizontal lines with a positive shift, and mostly horizontal lines with a negative shift. Mostly vertical lines with a positive shift may comprise lines corresponding to coordinates in the sinogram with a normal slope $\theta$ between $3\pi/4$ and $\pi$, mostly vertical lines with a negative shift may comprise lines corresponding to coordinates in the sinogram with the normal slope $\theta$ between 0 and $\pi/4$, mostly horizontal lines with a positive shift may comprise lines corresponding to coordinates in the sinogram with the normal slope $\theta$ between $\pi/2$ and $3\pi/4$, and mostly horizontal lines with a negative shift may comprise lines corresponding to coordinates in the sinogram with the normal slope $\theta$ between $\pi/4$ and $\pi/2$. Transitioning the sinogram to the linogram may comprise converting each coordinate (r, $\theta$) in the sinogram to a line (s, t) in the linogram according to:

$$\tan \theta = -(N/t)^p, r = sN/\sqrt{t^2+N^2}$$

wherein p equals one for mostly horizontal lines and p equals negative one for mostly vertical lines. The inverse Fast Hough Transform may be separately performed on each of the N×N images for each of the plurality of types of lines to produce a plurality of intermediate images. Producing the reconstructed CT image may comprise summing the plurality of intermediate images together.

Any of the methods may be embodied in executable software modules of a processor-based system, such as a server, and/or in executable instructions stored in a non-transitory computer-readable medium.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

In an embodiment, systems, methods, and non-transitory computer-readable media are disclosed for accelerated filtered back projection for CT image reconstruction that can reconstruct a CT image in $\Theta(N^2 \log N)$ addition operations and $\Theta(N^2)$ multiplication operations. This image reconstruction may be implemented as a software application embodying the algorithm disclosed herein.

After reading this description, it will become apparent to one skilled in the art how to implement the invention in various alternative embodiments and for alternative uses. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. Example Processing Device

Figure 1:
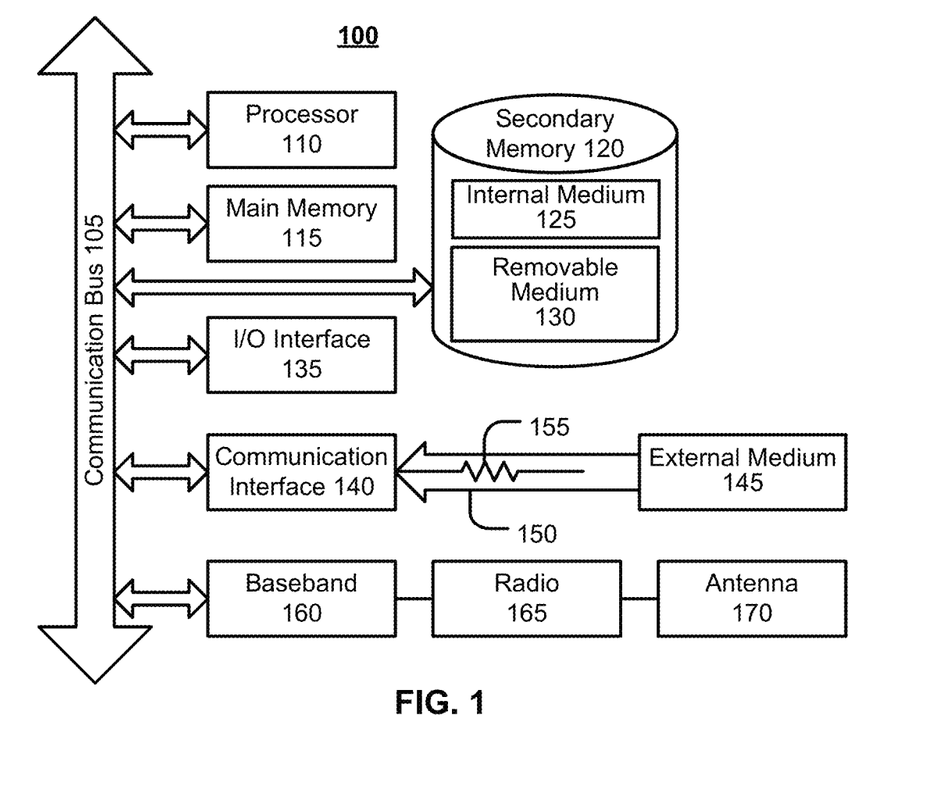
FIG. 1 illustrates an example processing system, by which one or more of the processes described herein, may be executed, according to an embodiment.

FIG. 1 is a block diagram illustrating an example wired or wireless system 100 that may be used in connection with various embodiments described herein. For example, system 100 may be used to execute one or more of the functions, processes, or methods described herein (e.g., one or more software modules of an application implementing the disclosed algorithm). System 100 can be a server (e.g., which services requests over one or more networks, including, for example, the Internet), a personal computer (e.g., desktop, laptop, or tablet computer), a mobile device (e.g., smartphone), a controller (e.g., in an autonomous vehicle, robot, etc.), or any other processor-enabled device that is capable of wired or wireless data communication. Other computer systems and/or architectures may be also used, as will be clear to those skilled in the art.

System 100 preferably includes one or more processors, such as processor 110. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 110. Examples of processors which may be used with system 100 include, without limitation, the Pentium® processor, Core i7® processor, and Xeon® processor, all of which are available from Intel Corporation™ of Santa Clara, California.

Processor 110 is preferably connected to a communication bus 105. Communication bus 105 may include a data channel for facilitating information transfer between storage and other peripheral components of system 100. Furthermore, communication bus 105 may provide a set of signals used for communication with processor 110, including a data bus, address bus, and/or control bus (not shown). Communication bus 105 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 100 preferably includes a main memory 115 and may also include a secondary memory 120. Main memory 115 provides storage of instructions and data for programs executing on processor 110, such as one or more of the functions, processes, and/or modules discussed herein. It should be understood that programs stored in the memory and executed by processor 110 may be written and/or compiled according to any suitable language, including without limitation C/C++, Java™, JavaScript™, Perl™, Visual Basic™,.NET™, and the like. Main memory 115 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 120 may optionally include an internal medium 125 and/or a removable medium 130. Removable medium 130 is read from and/or written to in any well-known manner. Removable storage medium 130 may be, for example, a magnetic tape drive, a compact disc (CD) drive, a digital versatile disc (DVD) drive, other optical drive, a flash memory drive, and/or the like.

Secondary memory 120 is a non-transitory computer-readable medium having computer-executable code (e.g., disclosed software modules) and/or other data stored thereon. The computer software or data stored on secondary memory 120 is read into main memory 115 for execution by processor 110.

In alternative embodiments, secondary memory 120 may include other similar means for allowing computer programs or other data or instructions to be loaded into system 100. Such means may include, for example, a communication interface 140, which allows software and data to be transferred from external storage medium 145 to system 100. Examples of external storage medium 145 may include an external hard disk drive, an external optical drive, an external magneto-optical drive, and/or the like. Other examples of secondary memory 120 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 100 may include a communication interface 140. Communication interface 140 allows software and data to be transferred between system 100 and external devices (e.g. printers), networks, or other information sources. For example, computer software or executable code may be transferred to system 100 from a network server via communication interface 140. Examples of communication interface 140 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 100 with a network or another computing device. Communication interface 140 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 140 are generally in the form of electrical communication signals 155. These signals 155 may be provided to communication interface 140 via a communication channel 150. In an embodiment, communication channel 150 may be a wired or wireless network, or any variety of other communication links. Communication channel 150 carries signals 155 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 115 and/or secondary memory 120. Computer programs can also be received via communication interface 140 and stored in main memory 115 and/or secondary memory 120. Such computer programs, when executed, enable system 100 to perform the various functions of the disclosed embodiments as described elsewhere herein.

In this description, the term "computer-readable medium" is used to refer to any non-transitory computer-readable storage media used to provide computer-executable code and/or other data to or within system 100. Examples of such media include main memory 115, secondary memory 120 (including internal memory 125, removable medium 130, and/or external storage medium 145), and any peripheral device communicatively coupled with communication interface 140 (including a network information server or other network device). These non-transitory computer-readable media are means for providing executable code, programming instructions, software, and/or other data to system 100.

In an embodiment that is implemented using software, the software may be stored on a computer-readable medium and loaded into system 100 by way of removable medium 130, I/O interface 135, or communication interface 140. In such an embodiment, the software is loaded into system 100 in the form of electrical communication signals 155. The software, when executed by processor 110, preferably causes processor 110 to perform one or more of the processes and functions described elsewhere herein.

In an embodiment, I/O interface 135 provides an interface between one or more components of system 100 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device, in the console of a vehicle, etc.).

In an embodiment, I/O interface 135 provides an interface to a camera (not shown). for example, system 100 may be a mobile device, such as a smartphone, tablet computer, or laptop computer, with one or more integrated cameras (e.g., rear and front facing cameras). Alternatively, system 100 may be a desktop or other computing device that is connected via I/O interface 135 to an external camera. In either case, the camera captures images (e.g., photographs, video, etc.) for processing by processor(s) 110 (e.g., executing the disclosed software) and/or storage in main memory 115 and/or secondary memory 120.

System 100 may also include optional wireless communication components that facilitate wireless communication over a voice network and/or a data network. The wireless communication components comprise an antenna system 170, a radio system 165, and a baseband system 160. In such an embodiment, radio frequency (RF) signals are transmitted and received over the air by antenna system 170 under the management of radio system 165.

In an embodiment, antenna system 170 may comprise one or more antennae and one or more multiplexors (not shown) that perform a switching function to provide antenna system 170 with transmit and receive signal paths. In the receive path, received RF signals can be coupled from a multiplexor to a low noise amplifier (not shown) that amplifies the received RF signal and sends the amplified signal to radio system 165.

In an alternative embodiment, radio system 165 may comprise one or more radios that are configured to communicate over various frequencies. In an embodiment, radio system 165 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 165 to baseband system 160.

If the received signal contains audio information, then baseband system 160 may decode the signal and convert it to an analog signal. Then, the signal is amplified and sent to a speaker. Baseband system 160 may also receive analog audio signals from a microphone. These analog audio signals may be converted to digital signals and encoded by baseband system 160. Baseband system 160 can also encode the digital signals for transmission and generate a baseband transmit audio signal that is routed to the modulator portion of radio system 165. The modulator mixes the baseband transmit audio signal with an RF carrier signal, generating an RF transmit signal that is routed to antenna system 170 and may pass through a power amplifier (not shown). The power amplifier amplifies the RF transmit signal and routes it to antenna system 170, where the signal is switched to the antenna port for transmission.

Baseband system 160 may also be communicatively coupled with processor 110, which may be a central processing unit (CPU). Processor 110 has access to data storage areas 115 and 120. Processor 110 is preferably configured to execute instructions (i.e., computer programs, such as the disclosed application, or software modules) that can be stored in main memory 115 or secondary memory 120. Computer programs can also be received from baseband processor 160 and stored in main memory 110 or in secondary memory 120, or executed upon receipt. Such computer programs, when executed, enable system 100 to perform the various functions of the disclosed embodiments.

2. Process Overview

Embodiments of processes for accelerated filtered back projection for CT image reconstruction will now be described in detail. It should be understood that the described processes may be embodied as an algorithm in one or more software modules, forming an application that is executed by one or more hardware processors processor 110, for example, as a software application or library. The described processes may be implemented as instructions represented in source code, object code, and/or machine code. These instructions may be executed directly by the hardware processor(s) 110, or alternatively, may be executed by a virtual machine operating between the object code and the hardware processor(s) 110. In addition, the disclosed application may be built upon or interfaced with one or more existing systems.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

Furthermore, while the processes, described herein, are illustrated with a certain arrangement and ordering of steps, each process may be implemented with fewer, more, or different steps and a different arrangement and/or ordering of steps. In addition, it should be understood that any step, which does not depend on the completion of another step, may be executed before, after, or in parallel with that other independent step, even if the steps are described or illustrated in a particular order.

2.1. Introduction

The most popular conventional approach to accelerate filtered back projection is based on the projection-slice or central-slice theorem, as disclosed in Potts et al., "New Fourier Reconstruction Algorithms for Computerized Tomography," Wavelet Applications in Signal and Image Processing VIII, Int'l Society for Optics and Photonics, 2000, 4119:13-23, which is hereby incorporated herein by reference as if set forth in full. Several algorithms use the Fast Fourier Transform (FFT) on an inhomogeneous grid, followed by a transition from polar coordinates to Cartesian coordinates in Fourier space using interpolation. In these cases, the quality of image reconstruction strongly depends on the chosen method of interpolation. A detailed analysis of artifacts that arise to distort the output image is provided by Potts et al., "Fourier Reconstruction of Functions from their Nonstandard Sampled Radon Transform," Journal of Fourier Analysis and Applications, 8(6):513-34, 2002, which is hereby incorporated herein by reference as if set forth in full. In addition, in Andersson, "Fast Inversion of the Radon Transform Using Log-Polar Coordinates and Partial Back-Projections," SIAM Journal on Applied Mathematics, 65(3): 818-37, 2005, which is hereby incorporated by reference as if set forth in full, the invariance properties of the Radon Transform and its dual were used to construct a method of inversion based on log-polar representations.

A completely different approach was reported in Basu et al., "$O(N^2 \log_2 N)$ Filtered Back-Projection Reconstruction Algorithm for Tomography," IEEE Transactions on Image Processing, 9(10):1760-73, 2000, and Xiao et al., "$O(N^2 \log N)$ Native Fan-Beam Tomographic Reconstruction," Proceedings IEEE Int'l Symposium on Biomedical Imaging, 2002, pp. 824-7, which are both hereby incorporated herein by reference as if set forth in full. In this approach, the main idea is not to reconstruct the whole image, but to use the properties of the Radon Transform to calculate sinograms corresponding to the four quadrants of the image, and then individually reconstruct the four quadrants. According to the Nyquist-Shannon theorem, only half projections are required to reconstruct a quadrant of the image without losing quality. Splitting of the image into quadrants can be continued sequentially until the size of the independently reconstructed sections reaches a value of one pixel. In this case, the algorithm requires $\Theta(N^2 \log N)$ multiplications. The shortcoming of this approach is a large number of intermediate interpolations, which can lead to the accumulation of errors, as described in Basu et al., "Error Analysis and Performance Optimization of Fast Hierarchical Back-projection Algorithms," IEEE Transactions on Image Processing, 10(7):1103-17, 2001, which is hereby incorporated herein by reference as if set forth in full.

Accordingly, in an embodiment, the disclosed application utilizes a new approach that reduces the computational complexity of the algorithm to $\Theta(N^2 \log N)$ addition operations and avoids Fourier space. To speed up the convolution, a ramp filter may be approximated by a pair of causal and anticausal recursive filters, also known as infinite impulse response (IIR) filters. The back projection may be performed with the fast discrete Hough Transform.

2.2. Filtered Back Projection

Figure 2A:
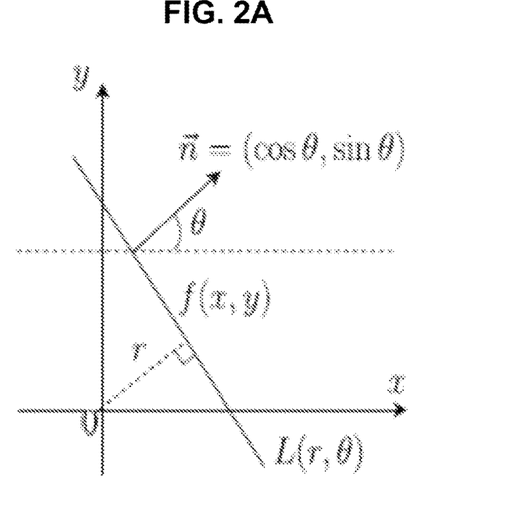
FIGS. 2A and 2B illustrate different parameterizations of straight lines on the plane, according to an embodiment, with FIG. 2A illustrating a parameterization of a line as a slope of the normal $\theta$ and the distance to the origin r, and FIG. 2B illustrating a parameterization of a line as an x- or y-intercept s and a horizontal or vertical shift t for mostly vertical lines $L_v$ and mostly horizontal lines $L_h$, respectively.

The basis of the FBP method will be briefly described. The Radon Transform defined on the space of straight lines L is the integral transform:

$$\mathcal{R}_{[f]}(L) = \int_L f(x,y) dl \qquad \text{Expression (1)}$$

wherein f (x, y) is some finite continuous function defined on the plane. In computed tomography, a straight line is usually given by the slope of the normal $\theta$ and the distance from the origin r, as illustrated in the (r, $\theta$)-parameterization in FIG. 2A. The projection of the function f (x, y) is the set of all points in its Radon Transform corresponding to a certain angle $\theta$:

$$p_\theta(r) = \mathcal{R}_{[f]}(\alpha,r)|_{\alpha=\theta} \qquad \text{Expression (2)}$$

The essence of the FBP method is the sequential application of two operations. In the first operation, the convolution of the projections with the Ram-Lak or ramp filtering function is performed, as disclosed in Ramachandran et al., "Three-dimensional Reconstruction from Radiographs and Electron Micrographs: Application of Convolutions Instead of Fourier Transforms," Proceedings of the National Academy of Sciences, 68(9):2236-40, 1971, which is hereby incorporated herein by reference as if set forth in full:

$$\tilde{p}_\theta(r) = p_\theta(r) * h(r) \qquad \text{Expression (3)}$$

wherein $$h(r) = \int_{-\infty}^{\infty} |\omega| e^{2\pi i \omega r} d\omega \qquad \text{Expression (4)}$$

In the second operation, conventional back projection is applied:

$$\tilde{f}(x,y) = \mathcal{B}_{[\tilde{p}]}(x,y) = \int_0^{2\pi} \tilde{p}_\theta(r) d\theta \qquad \text{Expression (5)}$$

wherein r=x cos $\theta$+y sin $\theta$.

In real measurement systems, it is not possible to obtain a continuous set of projections. Therefore, all integral operators are replaced by appropriate summation, and the continuous convolution is converted into one-dimensional linear filtering. In computed tomography, the number of projection angles P is chosen to be of the same magnitude as the image size N. In this case, convolution can be performed with $\Theta(N^3)$ operations in the image space or with $\Theta(N^2 \log N)$ operations using Fast Fourier Transform. The back projection requires $\Theta(N^3)$ operations.

Fast Recursive Filtering

Generally, an ideal ramp filter, with an impulse response given by Expression (4), has a singularity at the point r=0, as shown in Zeng, "Revisit of the Ramp Filter," 2014 IEEE Nuclear Science Symposium and Medical Imaging Conference (NSS/MIC), 2014, pp. 1-6, which is hereby incorporated herein by reference as if set forth in full. However, in real cases, the spectrum of measured projections is band-limited with the bandwidth 2W($|\omega|$<W). For a discrete signal, W=0.5/$\Delta$, where $\Delta$ is the sampling rate. Without loss of generality, $\Delta$ can be set equal to one (i.e., $\Delta$=1) by choosing the appropriate coordinate system. In this case, the impulse response of the discrete filter given by Expression (4) takes the form:

$$h(n) = 2\int_0^{1/2} |\omega|e^{2\pi i \omega n} d\omega = \frac{\sinc(\pi n)}{2} - \frac{\sinc^2(\pi n/2)}{4} \quad \text{Expression (6)}$$

wherein sin c(r)=sin (r)/r. Simplification of the latter expression yields:

$$h(n) = \begin{cases} 1/4, & n = 0 \\ 0, & n \text{ is even} \\ -1/(n\pi)^2, & n \text{ is odd} \end{cases} \quad \text{Expression (7)}$$

The discrete convolution of the projection $p_\theta$ with the kernel in Expression (7) can be recast as a finite impulse response (FIR) filter:

$$\tilde{p}_\theta(n) = p_\theta * h = \sum_{k=n-L_0}^{k=n+L_0} p_\theta(n-k)h(k) \quad \text{Expression (8)}$$

wherein L=2L$_0$+1 is the length of the filter kernel.

Even though the function h(n) decays quadratically with n, a decrease in the length of the filter kernel will lead to a significant distortion of the reconstructed image. To achieve the minimum error, the kernel length should be the same order of magnitude as N. Thus, although formally calculating the convolution of Expression (8) requires $\Theta(N^2)$ operations, in real cases, the factor for $N^2$ is very large. A reduction in the computational complexity of the convolution is essential for many signal-processing problems.

Deriche, "Using Canny's Criteria to Derive a Recursively Implemented Optimal Edge Detector," Int'l Journal of Computer Vision, 1(2):167-87, 1987, which is hereby incorporated herein by reference as if set forth in full, presented a group of computationally effective methods for approximating a Gaussian filter, including its first and second derivatives, using IIR filters. The difference expression that describes the discrete IIR filter has the form:

$$\tilde{p}_\theta(n) = \sum_{k=0}^{M-1} b_k p_\theta(n-k) - \sum_{k=1}^{Q} a_k \tilde{p}_\theta(n-k) \quad \text{Expression (9)}$$

wherein M and Q are the feedforward and feedback filter orders, and $a_k$ and $b_k$ are coefficients that characterize the filter. An advantage of the IIR filter is that for M«N and Q«N, only $\Theta(N^2)$ operations are required to process an image of size N×N. This is significantly less than for a FIR filter. Notably, the impulse response of the filter in Expression (7) is unidirectional, while the impulse response of the ramp filter is symmetric, i.e., r(n)=r(-n). A symmetric recursive filter can be represented as the sum of the causal and anticausal components, as described in Deriche, "Recursively Implementing the Gaussian and Its Derivatives," Tech. Rep., inria-00074778, 1993, which is hereby incorporated herein by reference as if set forth in full.

In an embodiment, the IIR filter is constructed so that its impulse response is equal to the impulse response of the FIR filter h(n). In this case, the impulse response in Expression (7) can be rewritten as the sum of causal and anticausal components:

$$h^+ = \begin{cases} h(0)/2, & n = 0 \\ h(n), & n > 0 \\ 0, & n < 0 \end{cases} \quad \text{Expression (10)}$$

$$h^- = \begin{cases} h(0)/2, & n = 0 \\ h(n), & n < 0 \\ 0, & n > 0 \end{cases}$$

Thus:

$$\tilde{p}_\theta = p_\theta * h^+ + p_\theta * h^- \quad \text{Expression (11)}$$

The resulting function $\tilde{p}_\theta$ can be presented as the sum of the outputs of two recursive filters:

$$\tilde{p}_\theta(n) = \tilde{p}_\theta^+(n) + \tilde{p}_\theta^-(n) \quad \text{Expression (12)}$$

where:

$$\tilde{p}_\theta^\pm(n) = \sum_{k=0}^{M-1} b_k^\pm p_\theta(n \mp k) - \sum_{k=1}^{Q} a_k^\pm \tilde{p}_\theta(n \mp k) \quad \text{Expression (13)}$$

Due to the symmetry, the coefficients $a_k^+ = a_k^-$ and $b_k^+ = b_k^-$. Thus, it is sufficient to determine the coefficients for only the causal filter. These coefficients can be found by minimizing the mean-square error between the impulse response of the FIR filter in Expression (8) and the IIR filter in Expression (9). Any optimization algorithm can be used. One such optimization algorithm is the Powell conjugate gradient method described in Powell, "An Efficient Method for Finding the Minimum of a Function of Several Variables without Calculating Derivatives," The Computer Journal, 7(2):155-62, 1964, which is hereby incorporated herein by reference as if set forth in full. Another such optimization algorithm is the simplex method described in Gao et al., "Implementing the Nelder-Mead Simplex Algorithm with Adaptive Parameters," Comput. Optim. Appl., 51(1):259-77, 2012, which is hereby incorporated herein by reference as if set forth in full. Notably, the above scheme can be applied, not only to the ramp filter, but to any filter used in the FBP approach, such as the filter used in Horbelt et al., "Discretization of the Radon Transform and of Its Inverse By Spline Convolutions," IEEE Transactions on Medical Imaging, 21(4):363-76, 2002, doi:10.1109/TMI.2002.1000260, which is hereby incorporated herein by reference as if set forth in full.

2.4. Fast Back Projection

An embodiment of the fast back projection that is used by the disclosed application will now be described.

2.4.1 Parameterization

In an embodiment, the original image plane of the CT image is parameterized into (s,t) space, such that a point $(x_0,y_0)$ on the original image plane (x,y) defines a line on the parameter plane (s,t). The set of projections in (s,t) space is sometimes called a linogram, as demonstrated in Edholm et al., "Linograms in Image Reconstruction from Projections," IEEE Transactions on Medical Imaging, 6(4):301-7, 1987, which is hereby incorporated herein by reference as if set forth in full.

Let function f (x,y) be given in the squared area of $0 \le x \le N$ and $0 \le y \le N$. The set of all lines can be divided into four classes:

(1) Mostly vertical lines with positive shift $L_v^+$ ($3\pi/4 \le \theta < \pi$);

(2) Mostly vertical lines with negative shift $L_v^-$ ($0 \le \theta < \pi/4$);

(3) Mostly horizontal lines with positive shift $L_h^+$ ($\pi/2 \le \theta < 3\pi/4$); and (4) Mostly horizontal lines with negative shift $L_h^-$ ($\pi/4 \le \theta \pi/2$).

Figure 2B:
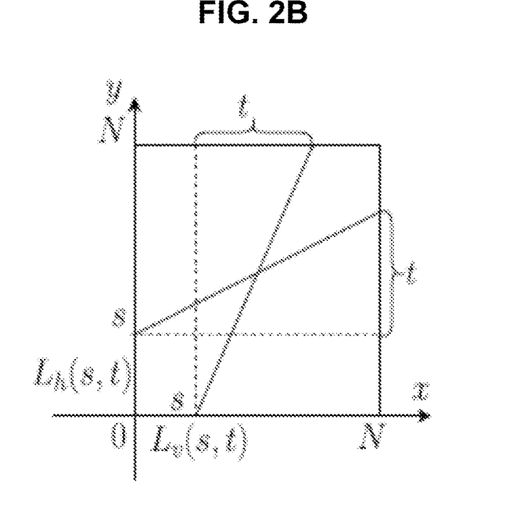

Parameters s and t specify the coordinates of two points of a line lying on the vertical boundary (for $L_h^\pm$) or horizontal boundary (for $L_v^\pm$), as illustrated in FIG. 2B. Parameter t takes values from $-N$ to 0 for $L_h^-$ and $L_v^-$, and from 0 to N for $L_h^+$ and $L_v^+$. Thus, the final linogram contains four N×N images for all types of lines.

2.4.2 Transition

In an embodiment, the original sinogram coordinates (r,θ) are transitioned to linogram coordinates (s,t). There is a one-to-one relationship between linogram coordinates (s,t) and the original sinogram coordinates (r,θ):

$$\tan \theta = -(N/t)^p, r = sN/\sqrt{t^2+N^2} \qquad \text{Expression (14)}$$

wherein p=1 for $L_h^\pm$ and p=-1 for $L_v^\pm$.

The transition from sinogram to linogram using linear interpolation only requires $\Theta(N^2)$ operations. However, a careless transition from (r,θ) to (s,t) variables can introduce an error related to the violation of the rotational invariance of the Radon Transform in (s,t) space, obtained for the squared image domain. Consider a projection in the linogram for $L_h^+$ with shift t. This projection in the linogram corresponds to a projection in the sinogram with an angle of inclination $\phi_t = \theta_t - \pi/2 = \arctan$ (t/N), as demonstrated by Expression (14). The length of the corresponding line is N/cos φ. Notably, this length is not constant and depends on the angle φ. Since the Radon Transform in the squared domain should preserve the Radon invariant (i.e., the sum of the values in any row is equal the total sum in the image), the projection amplitude is underestimated, relative to the conventional Radon Transform, which is equal to the sinogram obtained by the CT scanner, by a factor of $k_t=1/\cos \phi_t$. Thus, each linogram projection is "stretched" relative to the corresponding sinogram projection by the same factor $k_t$. Expressing the scaling coefficient explicitly yields:

$$k_t = \sqrt{1+t^2/N^2} \qquad \text{Expression (15)}$$

This parameter should be kept in mind when converting the linogram to the sinogram.

2.4.3 Back Projection

In an embodiment, back projection is performed in the (s,t) coordinate space. An important feature of (s,t) parameterization is morphological symmetry. In other words, each point in the original image corresponds to a straight line in the linogram, and each point in the linogram corresponds to a straight line in the original image. This morphological symmetry enables a connection to be established between the forward projection operator $\mathcal{R}$ [f](s,t) (i.e., Radon Transform) and the corresponding back projection operator $\mathcal{B}$ [p] (x,y). Parts of the linogram that correspond to the introduced classes of lines are denoted as $P_h^+(s,t)$, $P_h^-(s,t)$, $P_v^+(s,t)$, and $P_v^-(s,t)$. Notably, the forward projection operators for mostly horizontal lines $\mathcal{R}_h^\pm[f]$ can be obtained from the corresponding operators for mostly vertical lines $\mathcal{R}_v^\pm[f]$ by preliminary transposition of the image:

$$P_h^\pm(s,t) \mathcal{R}_h^\pm[f](s,t) = \mathcal{R}_v^\pm[f^T](s,t) \qquad \text{Expression (16)}$$

Rewriting the expressions from the forward projection operation in Expression (1) and the back projection operator in Expression (5) in (s,t) coordinates yields:

$$P_v^\pm(s,t) = \mathcal{R}_v^\pm[\tilde{f}](s,t) = \int_0^N \tilde{f}\left(s+\frac{t}{N}y, y\right)dy \qquad \text{Expression (17)}$$

$$\tilde{f}_v^\pm(x,y) = \mathcal{B}_v^\pm[P_v^\pm](x,y) = \pm \int_0^N P_v^\pm\left(y-\frac{x}{N}t, t\right)dt \qquad \text{Expression (18)}$$

Notably, comparing Expressions (17) and (18), the operator $\mathcal{B}_v^\pm$, which defines a mapping from (s,t) space to (x,y) space, can be expressed via the forward projection operator:

$$\mathcal{B}_v^\pm[P_v^\pm](x,y) = \pm \mathcal{R}_v^\pm[P_v^\pm](-x,y) \qquad \text{Expression (19)}$$

Thus, the back projection operation in (s,t) space is equivalent to the forward projection operation, except for the change in the sign of one of the parameters. Similarly, operator $\mathcal{B}_h^\pm$ can be expressed as:

$$\mathcal{B}_h^\pm[P_h^\pm](x,y) = \pm \{\mathcal{R}_h^\pm[P_h^\pm](-x,y)\}^T \qquad \text{Expression (20)}$$

2.4.4 Fast Hough Transform

In a discrete space, the Radon Transform of a function along a given line can be approximated by the sum of the function's values at points belonging to the discrete approximation of this line. With the appropriate choice of approximation, the time required to calculate the discrete projection operator can be significantly reduced. In Brady, "A Fast Discrete Approximation Algorithm for the Radon Transform," SIAM Journal of Computing, 27(1):107-19, 1998, which is hereby incorporated herein by reference as if set forth in full, it was noted that discrete representations of two lines with close slopes have a significant number of common points. In this case, there is no need to calculate the repeating section twice to find the sum along each of the two lines. Brady proposed sequentially calculating partial sums for segments of length $2^i$, i=1 . . . $\log_2(N+1)$.

Ershov et al., "Generalization of the Fast Hough Transform for Three-Dimensional Images," J. Comm. Technol. Electron., 63(6):626-36, 2018, doi:10.1134/S1064226918060074, which is hereby incorporated herein by reference as if set forth in full, presents a recursive implementation of the described algorithm for lines approximated by so-called dyadic patterns. This algorithm is also known as the Fast Hough Transform (FHT). In this implementation, the results are obtained separately for each type of line: $L_h^{\pm}$ and $L_v^{\pm}$. The computational complexity of the algorithm is $\Theta(N^2 \log N)$ operations. Moreover, all of these operations are summations, rather than multiplications.

In an embodiment, the disclosed application may utilize the asymptomatically fast simultaneous algebraic reconstruction technique (SART) algorithm, based on an implementation of the Fast Hough Transform, proposed in Prun et al., "A Computationally Efficient Version of the Algebraic Method for Computer Tomography," Automation and Remote Control, 74(10):1670-8, 2013, doi:10.1134/S000511791310007X, which is hereby incorporated herein by reference as if set forth in full.

2.4.5 Inverse Fast Hough Transform

According to Expressions (19) and (20), the back projection operator can be presented as a forward projection operator with the change in sign of one of the parameters. Consequently, in an embodiment, the disclosed application applies the Brady approach for back projection:

$$\tilde{f}_h^{\pm}(x,y) = \mathcal{B}[P_h^{\pm}(t,s)](-x,y), \tilde{f}_v^{\pm}(x,y) = \{\mathcal{B}[P_v^{\pm}(t,s)](-x,y)\}^T \quad \text{Expression (21)}$$

The final image reconstruction is the sum of four images:

$$\tilde{f}(x,y) = \tilde{f}_h^{+}(x,y) + \tilde{f}_h^{-}(x,y) + \tilde{f}_v^{+}(x,y) + \tilde{f}_v^{-}(x,y) \quad \text{Expression (22)}$$

2.5. Example Embodiment

In an embodiment, the disclosed application implements a fast algorithm to reconstruct an image from tomographic projections. Following an FBP strategy, an IIR filter is applied to an input sinogram with precalculated coefficients, to speed up the filtering operation. In addition, a Fast Hough Transform is used to speed up the back projection operation. Experimental results on the Shepp-Logan phantom demonstrate acceptable quality with a decrease in computational costs.

Figure 4:
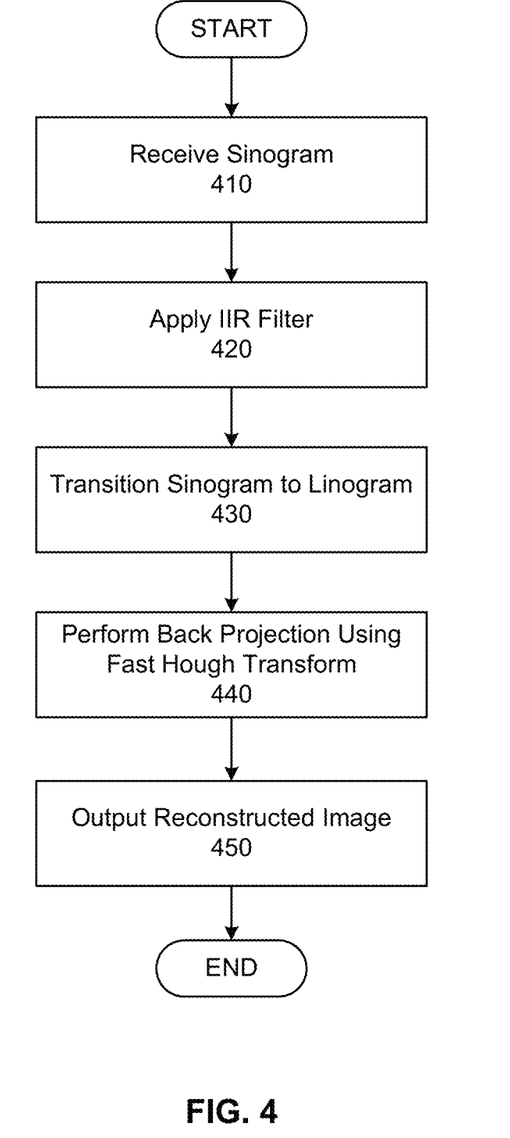
FIG. 4 illustrates an algorithm for image reconstruction, according to an embodiment.

FIG. 4 illustrates an algorithm for image reconstruction, according to an embodiment. Initially, a sinogram is received in step 410. In step 420, an IIR filter is applied to the sinogram. In step 430, the sinogram is transitioned or converted to a linogram. In step 440, a back projection is performed on the linogram using a Fast Hough Transform (i.e., an inverse Fast Hough Transform) to produce a reconstructed image. In step 450, the reconstructed image is output.

3. Experimental Results

Experimental results on simulated data demonstrate the efficiency of the approach of the disclosed application implementing the disclosed algorithm. In particular, experiments were conducted on the Shepp-Logan phantom, which is a standard test image that serves as a model of a human head in the development and testing of image reconstruction algorithms. The test images were reconstructed with FIR and IIR filters, using Q=M, N=512, and P=512. IIR filter coefficients were found using the simplex method.

Figure 3A:
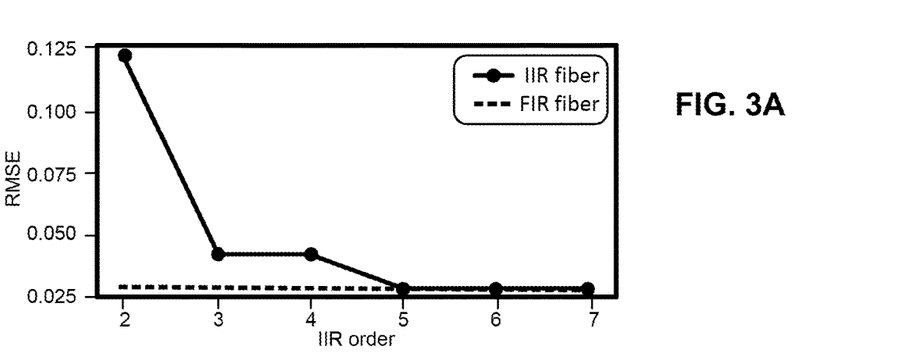
FIGS. 3A and 3B illustrate experimental results, according to an embodiment.
Figure 3B:
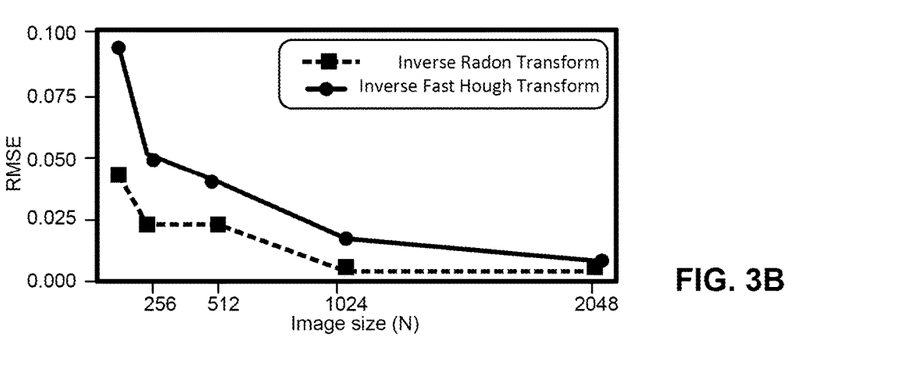

Two parts of the disclosed algorithm were investigated individually: (1) the root mean square error (RMSE) dependence on the IIR filter order, in which the Radon Transform is used for back projection; and (2) the dependence between RMSE and image size for Radon and Fast Hough back projection, in which the FIR filter is used for both the Radon and Fast Hough cases. FIG. 3A illustrates the difference in RMSE for IIR and FIR filters by IIR order, and FIG. 3B illustrates the difference in RMSE between the inverse Radon Transform and Fast Hough Transform by image size N, in the experimental results.

Figure 5A:
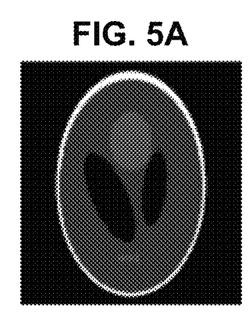
FIGS. 5A-5D illustrate examples of images that were reconstructed, according to an embodiment.
Figure 5B:
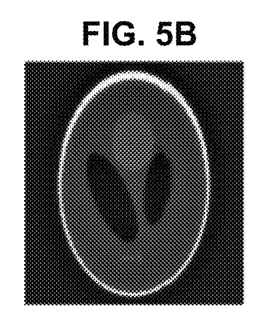
Figure 5C:
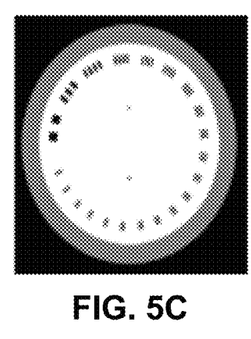
Figure 5D:
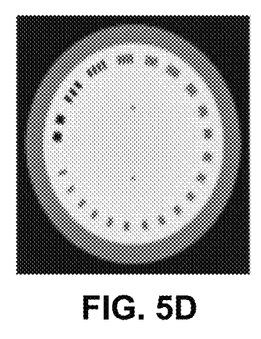

FIGS. 5A-5D illustrate examples of images that were reconstructed using the disclosed algorithm, wherein N=1024, P=1024, and Q=M=3. FIG. 5A illustrates the Shepp-Logan phantom, and FIG. 5B illustrates the image of the Shepp-Logan phantom that was reconstructed using an embodiment of the disclosed algorithm. Similarly, FIG. 5C illustrates the Catphan™ phantom, and FIG. 5D illustrates the image of the Catphan™ phantom that was reconstructed using an embodiment of the disclosed algorithm. Advantageously, the disclosed algorithm only requires $\Theta(N^2)$ operations for interpolation, filtering, and formation of the output images, and $\Theta(N^2 \log N)$ summations for back projection.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

What is claimed is:

1. A method comprising using at least one hardware processor to reconstruct a computed tomography (CT) image by:
    performing a filtered back projection on a sinogram, wherein back projection in the filtered back projection comprises
        transitioning the sinogram to a linogram using linear interpolation, wherein the linogram represents each line as two points (s, t) lying on boundaries of an N×N square area, wherein N is a linear size of the CT image, wherein the linogram comprises an N×N image for each of a plurality of types of lines, wherein the plurality of types of lines comprise mostly vertical lines with a positive shift, mostly vertical lines with a negative shift, mostly horizontal lines with a positive shift, and mostly horizontal lines with a negative shift, wherein mostly vertical lines with a positive shift comprise lines corresponding to coordinates in the sinogram with a normal slope θ between 3π/4 and π, mostly vertical lines with a negative shift comprise lines corresponding to coordinates in the sinogram with the normal slope θ between 0 and π/4, mostly horizontal lines with a positive shift comprise lines corresponding to coordinates in the sinogram with the normal slope θ between π/2 and 3π/4, and mostly horizontal lines with a negative shift comprise lines corresponding to coordinates in the sinogram with the normal slope θ between π/4 and π/2, and performing an inverse Fast Hough Transform on the linogram to produce the reconstructed CT image, and wherein filtering in the filtered back projection uses an infinite impulse response (IIR) filter.

2. The method of claim 1, further comprising using the at least one hardware processor to determine coefficients for the IIR filter by minimizing an error between an impulse response of the IIR filter and an impulse response of a finite impulse response (FIR) filter according to an optimization algorithm.

3. The method of claim 2, wherein the error is a mean-square error.

4. The method of claim 2, wherein the optimization algorithm comprises a simplex method.

5. The method of claim 2, wherein the optimization algorithm comprises a conjugate gradient method.

6. The method of claim 1, wherein transitioning the sinogram to the linogram comprises converting each coordinate (r, θ) in the sinogram to a line (s, t) in the linogram according to:

$$\tan\theta = -(N/t)^p, r = sN/\sqrt{t^2+N^2}$$

wherein p equals one for mostly horizontal lines and p equals negative one for mostly vertical lines.

7. The method of claim 1, wherein the inverse Fast Hough Transform is separately performed on each of the N×N images for each of the plurality of types of lines to produce a plurality of intermediate images.

8. The method of claim 7, wherein producing the reconstructed CT image comprises summing the plurality of intermediate images together.

9. A system comprising:
at least one hardware processor; and
one or more software modules configured to, when executed by the at least one hardware processor, reconstruct a computed tomography (CT) image by
performing a filtered back projection on a sinogram,
wherein back projection in the filtered back projection comprises
transitioning the sinogram to a linogram using linear interpolation, wherein the linogram represents each line as two points (s, t) lying on boundaries of an N×N square area, wherein N is a linear size of the CT image, wherein the linogram comprises an N×N image for each of a plurality of types of lines, wherein the plurality of types of lines comprise mostly vertical lines with a positive shift, mostly vertical lines with a negative shift, mostly horizontal lines with a positive shift, and mostly horizontal lines with a negative shift, wherein mostly vertical lines with a positive shift comprise lines corresponding to coordinates in the sinogram with a normal slope θ between 3π/4 and π, mostly vertical lines with a negative shift comprise lines corresponding to coordinates in the sinogram with the normal slope θ between 0 and π/4, mostly horizontal lines with a positive shift comprise lines corresponding to coordinates in the sinogram with the normal slope θ between π/2 and 3π/4, and mostly horizontal lines with a negative shift comprise lines corresponding to coordinates in the sinogram with the normal slope θ between π/4 and π/2, and performing an inverse Fast Hough Transform on the linogram to produce the reconstructed CT image, and wherein filtering in the filtered back projection uses an infinite impulse response (IIR) filter.

10. The system of claim 9, wherein transitioning the sinogram to the linogram comprises converting each coordinate (r, θ) in the sinogram to a line (s, t) in the linogram according to:

$$\tan\theta = -(N/t)^p, r = sN/\sqrt{t^2+N^2}$$

wherein p equals one for mostly horizontal lines and p equals negative one for mostly vertical lines.

11. A non-transitory computer-readable medium having instructions stored therein, wherein the instructions, when executed by a processor, cause the processor to reconstruct a computed tomography (CT) image by:
performing a filtered back projection on a sinogram,
wherein back projection in the filtered back projection comprises
transitioning the sinogram to a linogram using linear interpolation, wherein the linogram represents each line as two points (s, t) lying on boundaries of an N×N square area, wherein N is a linear size of the CT image, wherein the linogram comprises an N×N image for each of a plurality of types of lines, wherein the plurality of types of lines comprise mostly vertical lines with a positive shift, mostly vertical lines with a negative shift, mostly horizontal lines with a positive shift, and mostly horizontal lines with a negative shift, wherein mostly vertical lines with a positive shift comprise lines corresponding to coordinates in the sinogram with a normal slope θ between 3π/4 and π, mostly vertical lines with a negative shift comprise lines corresponding to coordinates in the sinogram with the normal slope θ between 0 and π/4, mostly horizontal lines with a positive shift comprise lines corresponding to coordinates in the sinogram with the normal slope θ between π/2 and 3π/4, and mostly horizontal lines with a negative shift comprise lines corresponding to coordinates in the sinogram with the normal slope θ between π/4 and π/2, and performing an inverse Fast Hough Transform on the linogram to produce the reconstructed CT image, and wherein filtering in the filtered back projection uses an infinite impulse response (IIR) filter.

12. The non-transitory computer-readable medium of claim 11, wherein transitioning the sinogram to the linogram comprises converting each coordinate (r, θ) in the sinogram to a line (s, t) in the linogram according to:

$$\tan\theta = -(N/t)^p, r = sN/\sqrt{t^2+N^2}$$

wherein p equals one for mostly horizontal lines and p equals negative one for mostly vertical lines.

* * * * *